United States Patent
Bhotla et al.

(10) Patent No.: US 9,822,070 B2
(45) Date of Patent: Nov. 21, 2017

(54) METHODS OF MANUFACTURE OF 2-HYDROCARBYL-3,3-BIS(HYDROXYARYL) PHTHALIMIDINES

(71) Applicant: SABIC GLOBAL TECHNOLOGIES B.V., Bergen Op Zoom (NL)

(72) Inventors: Venkata Ramanarayanan Ganapathy Bhotla, Karnataka (IN); Bhaskar Reddy Aluri, Bangalore (IN); S Shubashree, Karnataka (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/111,507

(22) PCT Filed: Jan. 14, 2015

(86) PCT No.: PCT/IB2015/050285
§ 371 (c)(1),
(2) Date: Jul. 14, 2016

(87) PCT Pub. No.: WO2015/107467
PCT Pub. Date: Jul. 23, 2015

(65) Prior Publication Data
US 2016/0340307 A1 Nov. 24, 2016

Related U.S. Application Data

(60) Provisional application No. 61/927,221, filed on Jan. 14, 2014.

(51) Int. Cl.
*C07D 209/46* (2006.01)
*C08G 64/12* (2006.01)
*B01J 27/125* (2006.01)

(52) U.S. Cl.
CPC .......... *C07D 209/46* (2013.01); *B01J 27/125* (2013.01); *C08G 64/12* (2013.01)

(58) Field of Classification Search
CPC .................................................. C07D 209/46

USPC ........................................ 528/208, 196, 198
See application file for complete search history.

(56) References Cited

U.S. PATENT DOCUMENTS

| | | |
|---|---|---|
| 6,429,212 B1 | 8/2002 | Hashimoto |
| 6,956,134 B2 | 10/2005 | Liu et al. |
| 7,041,774 B2 | 5/2006 | Kishan et al. |
| 7,045,482 B2 | 5/2006 | Chun et al. |
| 7,686,190 B2 | 3/2010 | Patrick |
| 7,838,689 B2 | 11/2010 | Bhotla et al. |
| 7,915,430 B2 | 3/2011 | Bhotla et al. |

FOREIGN PATENT DOCUMENTS

| | | |
|---|---|---|
| WO | 2006012162 A2 | 2/2006 |
| WO | 2013175448 A1 | 11/2013 |
| WO | 2014072923 A1 | 5/2014 |

OTHER PUBLICATIONS

Bordoloi et al., "Liquid-phase veratrole acylation and toluene alkylation over WOx/ZrO2 solid acid catalysts"; Journal of Molecular Catalysis A; Chemical 247 (2006), 58-64, p. 60.

Errera et al., "Sulla Condensazione Della Ftalide Col. Fenolo", Gazzetta Chimica Italiana, 1894, vol. 24, pp. 70-80, XP009183371, in Italian.

International Search Report for International Application No. PCT/IB2015/050285, International Application Filing Date Jan. 14, 2015; dated Apr. 1, 2015; 5 pages.

Koltunov et al., "Superacidic Activation of Maleimide and Phthalimide and Their Reactions With Cyclohexane and Arenes", Eur. J. Org. Chem., 2006, pp. 4861-4866.

Written Opinion for International Application No. PCT/IB2015/050285, International Application Filing Date Jan. 14, 2015; dated Apr. 1, 2015; 8 pages.

*Primary Examiner* — Terressa Boykin
(74) *Attorney, Agent, or Firm* — Cantor Colburn LLP

(57) ABSTRACT

A method for the manufacture of a 2-hydrocarbyl-3,3-bis(hydroxyaryl)phthalimidine composition comprises: reacting a phthalimide with a phenol in the presence of a catalyst and optionally a solvent at an elevated temperature to form the 2-hydrocarbyl-3,3-bis(hydroxyaryl)phthalimidine composition.

23 Claims, No Drawings

METHODS OF MANUFACTURE OF 2-HYDROCARBYL-3,3-BIS(HYDROXYARYL) PHTHALIMIDINES

CROSS REFERENCE TO RELATED APPLICATIONS

This application is a National Stage application of PCT/IB/50285, filed Jan. 14, 2015, which claims the benefit of U.S. Provisional Application No. 61/927,221, filed Jan. 14, 2014, both of which are incorporated by reference in their entirety herein.

BACKGROUND

This disclosure is directed to a method for the manufacture of 2-hydrocarbyl-3,3-bis(hydroxyaryl)phthalimidines, particularly to the manufacture of N-phenyl phenolphthalein bisphenol and N-methyl phenolphthalein bisphenol. This disclosure is also directed to the manufacture of polycarbonates from the prepared 2-hydrocarbyl-3,3-bis(hydroxyaryl)phthalimidines.

2-Hydrocarbyl-3,3-bis(hydroxyaryl)phthalimidines such as N-phenyl phenolphthalein bisphenol (PPPBP) can be used in the manufacture of homopolycarbonates and copolycarbonates. Commercially, PPPBP is synthesized from aniline and phenolphthalein in the presence of hydrogen chloride. The staring material, phenolphthalein, can be manufactured from phthalic anhydride and phenol.

There are several challenges associated with the commercial process. For example, crude PPPBP obtained via this process typically contains aminophenol impurity, 2-aryl-3-(aminoaryl-3-(hydroxyaryl)phthalimidine, which must be removed through several activated carbon treatments. Final purification is conducted by a trituration using a methanol/water solvent system to bring the phenolphthalein within specification limits and to improve the color of the monomer. This multistep purification process uses large amount of activated carbon which is recycled only for few cycles and hence generates waste. In addition, the multistep purification process involves multiple unit operations which lead to yield losses.

Accordingly, it would be desirable to develop a process for the preparation of 2-hydrocarbyl-3,3-bis(hydroxyaryl) phthalimidine that reduces or avoids formation of aminophenol impurity and waste generation, for example by avoiding the use of activated carbon. It would also be desirable if this process provides 2-hydrocarbyl-3,3-bis(hydroxyaryl)phthalimidine of high yield and purity.

SUMMARY

Disclosed herein is a method for the manufacture of a 2-hydrocarbyl-3,3-bis(hydroxyaryl)phthalimidine composition. The method comprises reacting a phthalimide of formula (2) with a phenol of formula (3)

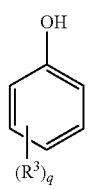
(2)

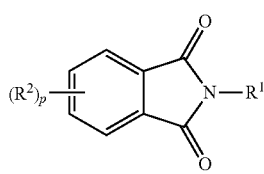
(3)

in the presence of a catalyst and optionally a solvent at an elevated temperature to form the 2-hydrocarbyl-3,3-bis(hydroxyaryl)phthalimidine composition, wherein the 2-hydrocarbyl-3,3-bis(hydroxyaryl)phthalimidine composition comprises a 2-hydrocarbyl-3,3-bis(hydroxyaryl)phthalimidine of formula (1)

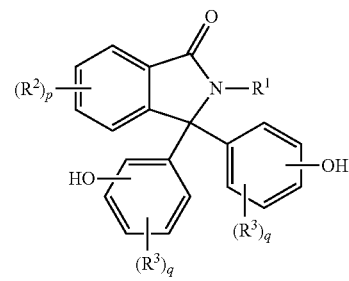
(1)

wherein in formulas (1), (2) and (3), $R^1$ is hydrogen, $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are independently 0 to 4.

Also disclosed is a method for the manufacture of a polycarbonate comprising:

reacting a phthalimide of formula (2) with a phenol of formula (3)

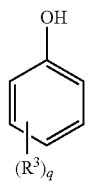
(2)

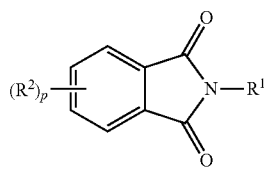
(3)

in the presence of a catalyst and optionally a solvent at an elevated temperature to form a 2-hydrocarbyl-3,3-bis(hydroxyaryl)phthalimidine composition comprising a 2-hydrocarbyl-3,3-bis(hydroxyaryl)phthalimidine of formula (1)

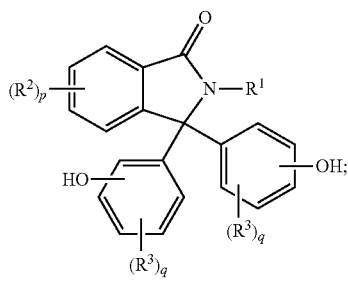

(1)

polymerizing the 2-hydrocarbyl-3,3-bis(hydroxyaryl) phthalimidine of formula (1) and optionally a bisphenol different from the 2-hydrocarbyl-3,3-bis(hydroxyaryl) phthalimidine of formula (1) to form the polycarbonate, wherein in formulas (1), (2) and (3), $R^1$ is hydrogen, $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are independently 0 to 4.

A 2-hydrocarbyl-3,3-bis(hydroxyaryl)phthalimidine and a polycarbonate manufactured by the above methods are also provided.

The above described and other features are exemplified by the following Detailed Description and Examples.

DETAILED DESCRIPTION

The inventors hereof have developed a simplified, novel route to prepare 2-hydrocarbyl-3,3-bis(hydroxyaryl)phthalimidines. Specifically, PPPBP can be synthesized by reacting phenol with N-phenylphthalimide (NPP) in the presence of a catalyst such as aluminum chloride at an elevated temperature. Depending on the solvent used for the reaction, either 2-phenyl-3-(4-hydroxyphenyl)-3-(2-hydroxyphenyl)phthalimidine (o,p'-PPPBP) or 2-phenyl-3,3-bis(4-hydroxyphenyl)phthalimidine (p,p'-PPPBP) can be obtained as the major product of the reaction. For example, when 1,1,2,2-tetrachloroethane is used, the reaction yields o,p'-PPPBP as the major product, while when 1,2-dichlorobenzene is used, the reaction provides p,p'-PPPBP as the major product. Starting material NPP in turn can be prepared by reacting phthalic anhydride with aniline in near quantitative yield and greater than 99.7% purity. In this synthesis method inventors hereof have not observed any aminophenol formation. Accordingly, the method has the advantage of avoiding multistep charcoal treatments, thus reducing the generation of carbon waste and simplifying the downstream purification process.

In an embodiment, described herein is a method for the manufacture of a 2-hydrocarbyl-3,3-bis(hydroxyaryl) phthalimidine composition. The 2-hydrocarbyl-3,3-bis(hydroxyaryl)phthalimidine composition comprises a 2-hydrocarbyl-3,3-bis(hydroxyaryl)phthalimidine of formula (1)

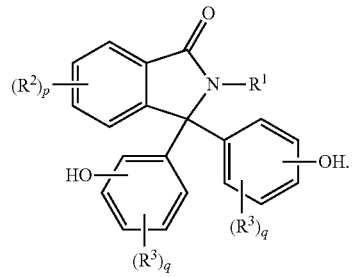

(1)

The method comprises reacting a phthalimide of formula (2) with a phenol of formula (3)

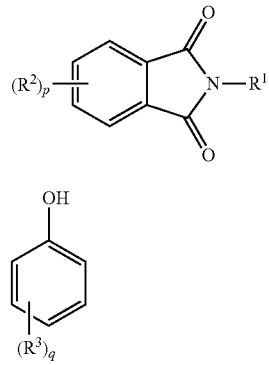

(2)

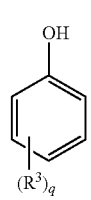

(3)

in the presence of a catalyst and optionally a solvent at an elevated temperature.

In formulas (1), (2) and (3), $R^1$ is hydrogen, $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are each independently 0 to 4, for example 0 to 2, 0 to 1, or 0. In a specific embodiment, p and q are each 0 and $R^1$ is phenyl or methyl, preferably methyl.

The reaction is carried out using a stoichiometric excess of the phenolic compound relative to the phthalimide compound. In an embodiment, the reaction is carried out using a molar ratio of the phenol of formula (3) to the phthalimide of formula (2) of greater than 2, 2 to 10, 3 to 6 or 3 to 5.

The catalyst can be an ionic liquid catalyst composition as described in U.S. Pat. No. 7,838,689. The ionic liquid catalyst composition is formed by combining an ionic liquid and a metal halide. It is to be understood that the "ionic liquid catalyst composition" as used herein means the combination of the ionic liquid and the metal halide, and may or may not contain the ionic liquid and/or metal halide as individual constituents.

An "ionic liquid" as used herein means a salt having a melting point below 100° C., specifically below 50° C., and even more specifically at 23° C. (room temperature), and at about 1 atmosphere of pressure. The ionic liquids comprise a cation ionically associated with an anion. The cations are generally relatively large compared to simpler organic or inorganic cations, and contribute to the low melting point of the ionic liquids. Often, the cations are asymmetric, heterocyclic organic cations such as imidazolium, pyrazolium, pyridinium, pyrazinium, pyrimidinium, $C_1$-$C_{32}$ tetraalkylphosphonium, and $C_1$-$C_{32}$ tetraalkylammonium cations. The anions are generally smaller, and can be organic or inorganic, for example formate or a halide.

In a specific embodiment, the ionic liquid is an imidazolium salt of formula

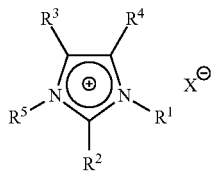

wherein $R^1$ and $R^5$ are each independently a $C_1$-$C_{12}$ hydrocarbyl group, $R^2$, $R^3$, and $R^4$ are each independently a hydrogen or $C_1$-$C_{12}$ hydrocarbyl group, and $X^-$ is anion. In an embodiment, $R^1$ and $R^5$ are each a $C_1$-$C_{12}$ alkyl group, and $R^2$, $R^3$, and $R^4$ are each independently a hydrogen atom or an alkyl group, specifically an alkyl having from 1 to 6 carbon atoms, more specifically from 1 to 4 carbon atoms. In an embodiment, each of $R^1$, $R^2$, $R^3$, $R^4$, and $R^5$ is methyl.

Some specific examples of such imidazolium salts include 1-alkyl-3-methyl-imidazolium salts such as 1-butyl-3-methyl-imidazolium chloride or 1-ethyl-3-methyl-imidazolium chloride.

In other embodiments, the ionic liquid is a pyrazolium salt of formula:

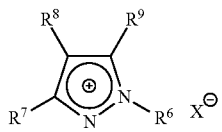

wherein $R^6$ is a $C_1$-$C_{12}$ hydrocarbyl group, and $R^7$, $R^8$, and $R^9$ are each independently a hydrogen atom or a $C_1$-$C_{12}$ hydrocarbyl group, and $X^-$ is an anion.

In a specific embodiment, the ionic liquid comprises a pyrazolium cation wherein $R^6$ is an alkyl group, specifically an alkyl having from 1 to 8 carbon atoms, more specifically from 1 to 6 carbon atoms, even more specifically from 1 to 4 carbon atoms; and $R^7$, $R^8$, and $R^9$ are each independently a hydrogen atom or an alkyl group, specifically an alkyl having from 1 to 6 carbon atoms, and more specifically from 1 to 4 carbon atoms.

Another example of an ionic liquid used in making the ionic liquid catalyst composition is a pyridinium salt of formula

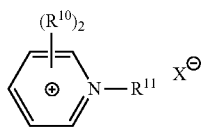

wherein $R^{11}$ is a $C_1$-$C_{12}$ hydrocarbyl group, each $R^{10}$ is independently hydrogen or a $C_1$-$C_{12}$ hydrocarbyl group, and $X^-$ is an anion. A specific example of such an ionic liquid is N-butyl pyridinium chloride.

Still other examples of ionic liquids are pyrimidinium salts or pyrazinium salts of formulas

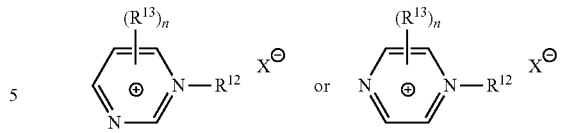

wherein $R^{12}$ is a $C_1$-$C_8$ hydrocarbyl group; each $R^{13}$ is independently hydrogen or a $C_1$-$C_{12}$ hydrocarbyl group, n is 1 to 4, and $X^-$ is an anion.

In the pyrimidinium and pyrazinium salts, $R^{12}$ is specifically an alkyl group, specifically an alkyl having from 1 to 8 carbon atoms, and each $R^{13}$ is independently a hydrogen atom or an alkyl, specifically an alkyl having from 1 to 6 carbon atoms.

Still other examples of ionic liquids for use in the ionic liquid catalyst composition are ammonium and phosphonium salts of formulas

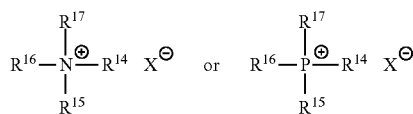

wherein $R^{14}$, $R^{15}$, $R^{16}$, and $R^{17}$ are each independently a $C_1$-$C_{12}$ hydrocarbyl group and $X^-$ is an anion.

Examples of these types of ionic liquids include tetraalkyl ammonium salts and tetraalkyl phosphonium salts, wherein each $R^{14}$, $R^{15}$, $R^{16}$, and $R^{17}$ is each the same alkyl group, specifically an alkyl having from 1 to 8 carbon atoms. Certain members of these classes possess ionic liquids properties similar to those of the organic cyclic cations.

The ionic liquid catalyst composition also comprises a combination comprising at least one of the foregoing ionic liquids.

In specific embodiments, the ionic liquid catalyst composition comprises an ionic liquid that is a heterocyclic imidazolium or pyridinium salt, specifically a 1,3-alkylimidazolium salt or an N-alkyl pyridinium salt, or a combination comprising at least one of the foregoing salts, wherein each alkyl group independently has 1 to 6 carbon atoms.

The anion ($X^-$) in the foregoing salts is an inorganic or organic anion, for example a tetrafluoroborate, nitrate, hexafluorophosphate, perchlorate, halide, phosphate, acetate, triflate (trifluoromethane sulfonate), sulfonate, methyl sulfonate, carboxylate, bis-trifluoromethyl sulfonamide, or a combination comprising at least one of the foregoing inorganic anions. More specifically, the inorganic anion is a halide, particularly when the cation is a 1,3-alkylimidazolium or an N-alkyl pyridinium.

The ionic liquids are prepared by a number of different methods known in the art. For example, 1-butyl-3-methyl-imidazolium chloride is prepared by boiling commercially available 1-methylimidazole with a 1-haloalkane such as 1-chlorobutane, followed by cooling, to obtain 1-butyl-3-methylimidazolium chloride. Similar preparation methods are employed to form other ionic liquids. For example a 1-alkyl-3-methylimidazolium bromide salt is prepared by heating 1-methylimidazole with a 1-bromoalkane, followed by cooling. To form a salt with a different anion, the 1-alkyl-3-methylimidazolium bromide salt, for example, is dissolved in a suitable water-insoluble organic solvent such as dichloromethane, and agitated in the presence of an aqueous solution of the sodium salt of the desired anion, such as tetrafluoroborate ion. If the 1-alkyl group of the 1-alkyl-3-methylimidazolium cation is longer than about five carbons, the cation will remain in association with the dichloromethane, while the bromide ion will tend to migrate to the aqueous solution and be replaced by the tetrafluoroborate ion to maintain charge balance. This process avoids the necessity for an ion exchange column. The dichloromethane is removed by evaporation, if desired, to yield the pure 1-alkyl-3-methylimidazolium tetrafluoroborate salt.

Different metal halides are used to form the ionic liquid catalyst compositions. In some embodiments, the metal in the metal halide is a Group IIB, IIIA, VIII, or IVA metal such as aluminum, iron, zinc, tin, or lead, and is specifically zinc. The halide is selected from any of fluoride, chloride, bromide, iodide, or a combination thereof, and is specifically chloride, e.g., $AlCl_3$ or $FeCl_3$. In an embodiment, zinc chloride is used.

The ionic liquid catalyst composition is obtained by simply combining the ionic liquid with the metal halide, preferably with agitation and at an elevated temperature. For example, the ionic liquid and the metal halide are mixed under an inert gas at 50 to 150° C. for 1 to 24 hours. The metal halide, typically a solid, dissolves gradually in the reaction mass to form a clear viscous liquid that is subsequently cooled and dried.

The molar ratio of the ionic liquid, specifically a quaternary ammonium salt, to the metal halide, specifically zinc chloride, can be 1:1 to 1:3. More specifically the molar ratio of the ionic liquid, specifically a quaternary ammonium salt, to the metal halide, specifically zinc chloride, can be 1:1.8 to 1:2.2.

A promoter may be used together with the ionic liquid catalyst composition. Exemplary promoters include chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, and combinations comprising at least one of the foregoing promoters. Specific promoters that can be used include chlorosulphonic acid, methanesulphonic acid, dodecylbenzenesulphonic acid, triflic acid, boron trifluoride, p-toluene sulphonyl chloride, and combinations comprising at least one of the foregoing. In an embodiment, the promoter is chlorosulphonic acid.

The amount of the ionic liquid catalyst composition used in the reaction varies, depending on the type of ionic liquid catalyst composition, its activity, the desired time for the reaction, and like considerations. In general, the amount of the ionic liquid catalyst composition is 25 to 100 wt. %, based on the total weight of the phthalimide of formula (2) and the phenol of formula (3). Other components in the reaction mixture, in addition to the ionic liquid and the metal halide, dissolve in the ionic liquid catalyst composition, such as the promoter or organic solvents, but are excluded for determining weight percent. More specifically, the ionic liquid catalyst composition is present in an amount of 25 to 75 wt. % based on the weight of phthalimide and the phenolic compound.

The promoter is present in the amount of up to 0.01 to 0.6 molar equivalents, based on the moles of phthalimide. Specifically, chlorosulphonic acid is present in an amount of 0.05 to 0.5 molar equivalents, more specifically 0.1 to 0.3 molar equivalents, based on the moles of phthalimide.

The heterogeneous catalyst comprises a calcined product of a heteropolyacid composition on a porous support. A heteropolyacid is an oxygen-containing inorganic polyacid that contains molybdenum (Mo), tungsten (W), vanadium (V), niobium (Nb), and the like as a polyatom, and phosphorous (P), silicon (Si), germanium (Ge), boron (B), cobalt (Co), and the like as a central heteroatom. In an embodiment, a central phosphorous or silicon atom connects twelve peripheral octahedrally coordinated metal atoms. A "heteropolyacid composition" as used herein is inclusive of both the acid form and the corresponding salt, wherein one or more of the acidic hydrogens in the acid is replaced by a cation, for example an alkali metal, an alkaline earth metal, an ammonium ion, a $C_{1-8}$ tetraalkyl ammonium ion, and the like. A combination of cations can be used. More specifically, in an embodiment, the heterogeneous catalyst comprises a heteropolyacid composition containing molybdenum, tungsten, vanadium or combinations comprising at least one of the foregoing metals as the polyatom, and phosphorous or silicon as a central heteroatom. In an embodiment, mixtures of metals are employed in the heteropolyacid composition, for example, both a molybdenum and a tungsten metal. In another specific embodiment, the porous support is a mixture of a metal oxide with another material, for example, an aluminosilicate zeolite.

In another embodiment, the catalyst is a heteropolyacid composition as described in U.S. Pat. No. 7,868,190. The composition comprises a heteropolyacid (or the corresponding salt) of formula $(H)_n(M^4)(M^5)_{12}O_{40}$ wherein n is 3, 4, 5, or 6, $M^4$ is phosphorus or silicon, and $M^5$ is tungsten, molybdenum, or a combination comprising at least one of the foregoing metals. When $M^4$ is phosphorus, n is 3 and when $M^4$ is silicon, n is 4. For example, the supported heterogeneous catalyst comprises at least one heteropolyacid composition comprising silicotungstic acid, tungstophosphoric acid, molybdophosphoric acid, and precursors thereof, or combinations comprising at least one of the foregoing heteropolyacids, or their corresponding salts. Heteropolyacids can include both tungsten and molybdenum, for example, molybdotungstophophoric acid ($H_3PMo_{12-x}W_xO_{40}$, wherein x is 1 to 12).

In a specific embodiment, the heteropolyacid composition comprises silicotungstic acid, silicomolybdic acid, tungstophosphoric acid, molybdophosphoric acid, or a combination comprising at least one of the foregoing acids, or their corresponding salts.

In another embodiment, the heteropolyacid includes other metals in addition to molybdenum or tungsten. In an embodiment, a heteropolyacid composition is of formula:

$(M^6)(M^7)(M^8)_{12}O_{40}$ wherein $M^6$ is a Group III element (boron, aluminum, or the like); $M^7$ is phosphorus or silicon, and $M^8$ is tungsten or molybdenum.

In still another embodiment, the heteropolyacid is of formula $H_{3+n}(M^7)V_n(M^8)_{12-n}O_{40}$ wherein n is 0 to 4, and $M^7$ and $M^8$ are as defined above. For example, such heteropolyacids can include 12-molybdotungstophosphoric acid ($H_{3+x}PMo_{12-x}W_xO_{40}$, wherein x is 0 to 12), 18-molybdovanadophosphoric acid ($H_{6+x}P_2Mo_{18-x}V_xO_{62}$, wherein x is 0 to 18), 18-tungstoniobiophosphoric acid, and the like.

A heteropolyacid and/or its salt can be purchased or prepared by known methods, for example, as disclosed in U.S. Pat. No. 7,045,482 or U.S. Pat. No. 6,956,134. Heteropolyacids are also commercially available from E-Merck, for example.

The metals in the calcined catalyst (calcined heteropolyacid composition) or in the support are not limited to any particular valence states. These metals can be present in the catalyst or support in any possible positive oxidation for the metal species. "Metal oxide" as used herein means compositions comprising the metal oxide, which may or may not further comprise the corresponding metal hydroxides and/or waters of hydration. Thus, a "metal oxide" refers qualitatively to compositions wherein an elemental analysis reveals the presence of the relevant metal (in one or more valence states) and oxygen. For example, an exemplary porous support disclosed herein is zirconia, having formula ZrO(OH)$_x$. As is understood by those of skill in the art, the amount of oxygen measured in such an analysis will depend on a number of factors such as the valence state of the metal, for example a Group IVB or Group VIB metal, moisture content, and the like. For convenience, the porous supports can be referred to herein using formulas such as $XO_2$ wherein, for example, X is a Group IVB metal such as zirconium. It will be appreciated, however, that this notation is for convenience, and metal oxides as represented by $XO_2$ may comprise the corresponding hydroxides and/or contain waters of hydration. Thus, the heterogeneous catalysts described herein are not subject to a single specific formula for every embodiment.

Various porous materials that can be used as the support include, for example, zirconia (zirconium oxide, $ZrO_2$), titania (titanium oxide, $TiO_2$ (anatase or rutile)), ceria (cerium oxide, $CeO_2$), aluminosilicates, silica (silicon dioxide, $SiO_2$), alumina, (aluminum oxide, $Al_2O_3$ (acidic or neutral)), zinc oxide, magnesia (magnesium oxide, MgO), niobium oxide, tin oxide, and combinations comprising at least one or more of the foregoing materials. Aluminosilicates, for example, can include various zeolites such as the SBA series of zeolites, for example, SBA-11, SBA-12, and SBA-15. Other exemplary types of zeolites include mordenite, ZSM-5, L-zeolite, faujasite, ferrierite, and chabazite. In one specific embodiment, the support is zirconia.

In one specific embodiment, the heteropolyacid composition comprises tungsten and the porous support comprises zirconia. Specific embodiments include, for example, supported heterogeneous catalysts in which the heteropolyacid composition that is used and the porous support are, respectively, silicotungstic acid and zirconia, tungstophosphoric acid and zirconia, tungstophosphoric acid and titania, tungstophosphoric acid and both zirconia and aluminosilicate, and a combination comprising at least one of the foregoing pairs or groups of heteropolyacid composition and porous support.

In various embodiments, the porous support is a microporous or a mesoporous material. Mesoporous supports have a pore size of greater than or equal to about 10 to about 100 angstroms, and the microporous supports have a pore size of less than or equal to about 10 angstroms, as determined by BET measurements. The supported heterogeneous catalyst has a surface area of 100 to 750 m$^2$/g, specifically 300 to 600 m$^2$/g measured in accordance with the BET method. The surface density of the tungsten or molybdenum (or both) in the supported heterogeneous catalyst is 0.1 to 5, specifically 1 to 2.5, atoms per nanometer square area, as determined according to the method of A Bordoloi et al, *Journal of Molecular Catalysis A; Chemical* 247 (2006) 58-64, page 60.

The surface density of the metal on the supported heterogeneous catalyst, expressed as the number of metal atoms per nanometer square meter (metal atoms per nm$^2$) is calculated based on the heteropolyacid loading and surface area, using the equation:

Surface density of metal={[heteropolyacid loading wt. %/100]×6.023×10$^{23}$}/{(formula weight of heteropolyacid)×BET surface area (m$^2$ g/1× 10$^{18}$)}.

The supported heterogeneous catalysts are made by a variety of methods. In an embodiment, employing incipient wetness impregnation of a support or support precursor with a methanolic solution of the heteropolyacid compound, the catalyst is dispersed over the surface of the support or a support precursor, and the amounts are chosen so as to achieve the desired surface density. Thermal treatment of the catalyst and support is carried out to make the final supported heterogeneous catalyst.

In an embodiment, when using a zirconia support, the supported catalyst is made by wet impregnation of zirconium oxyhydroxide with a heteropolyacid composition. Zirconium oxyhydroxide is prepared by dissolving zirconium oxychloride in distilled water, after which sufficient aqueous ammonia is added to precipitate zirconium hydroxide. After the precipitate is separated, washed, and dried, the product is impregnated with a solution of the heteropolyacid. After removing excess water and drying in an oven, the dried material is calcined with heating to obtain the supported heterogeneous catalyst.

The surface area of the supported heterogeneous catalyst is influenced by both the support and catalyst. For example, it has been found that pure zirconium oxyhydroxide dried at 120° C. showed a surface area of about 330 m2 per gram. After calcination at 800° C., the surface area decreased to 10 m2 per gram. Addition of catalyst to the support can increase the surface area in some embodiments. Without wishing to be bound by theory, this might be explained by the catalyst interacting with the zirconia support to inhibit sintering and stabilizing the tetragonal phase of zirconia, which leads to an increase in surface area. However, higher loadings of catalyst can cause the formation of crystalline metal oxide such as tungsten oxide that can plug the pores and decrease the specific surface area.

In some embodiments, the X-ray diffraction (XRD) pattern of the supported catalysts showed that the presence of the heteropolyacid catalyst can influence the crystallization of zirconium oxyhydroxide into zirconia. Pure zirconia calcined at 750° C. is mainly monoclinic with only a small amount of the tetragonal phase. The tetragonal phase becomes dominant with about 15 wt. % heteropolyacid catalyst. For lesser amounts of heteropolyacid catalyst compositions, the XRD pattern is more of a sum of the monoclinic and tetragonal phases of zirconia. The tetragonal content of zirconia at a fixed loading depends on the calcination temperature. In an embodiment, the zirconia in the catalyst comprises greater than 10, up to 100 volume percent (vol. %) of tetragonal zirconia, specifically, 50 to 100 vol. %, more specifically 80 to 100 vol. % of tetragonal zirconia, all based on XRD analysis. At less than 25 wt. % heteropolyacid catalyst loading, and less than 850° C. calcination, no diffraction lines or only a slight indication can be attributed to crystalline WO$_3$ in bulk from tungsten-containing heteropolyacids. Without being bound by theory, this may indicate decreased dispersion of catalyst on the support.

In another embodiment, a supported heterogeneous catalyst is obtained by reacting a heteropolyacid composition with a functionalized zeolite composition, as disclosed, for example, in U.S. Pat. No. 7,041,774 B2. In an embodiment, a solution of the heteropolyacid in a suitable solvent is treated with a functionalized zeolite, for example, having sulphonic acid or mercapto groups, followed by evaporation of the solvent and calcination to furnish the heteropolyacid-functionalized zeolite. Suitable solvents used for reaction with the heteropolyacid include water and $C_1$ to $C_8$ alcohols, such as methanol, ethanol, isopropanol, and n-butanol. Thus, structural units of a heteropolyacid are covalently linked to a porous support.

The amount of heteropolyacid used in the heterogeneous catalyst varies, depending on the type of heteropolyacid, the type of support, the desired activity of the heterogeneous catalyst, and like consideration. For example, the total amount of the heteropolyacid is 5 to 70 wt. %, specifically 10 to 30 wt. %, based on the weight of the support.

In another embodiment, the catalyst can be a heterogeneous catalyst as described in U.S. Pat. No. 7,915,430. The catalyst comprises a metal oxide in combination with a porous support. The metal oxide comprises molybdenum, tungsten, or a combination comprising at least one of molybdenum and tungsten. The porous support is another metal oxide, for example zirconium oxide, cerium oxide, or other oxide such as silica.

In another embodiment, the heterogeneous catalyst comprises a sulfated metal oxide support, in particular a sulfated zirconium oxide.

The metals in the catalyst or in the support are not limited to any particular valence state. These metals can be present in the catalyst or support in any possible positive oxidation for the metal species. "Metal oxide" as used herein means compositions comprising the metal oxide, which may or may not further comprise the corresponding metal hydroxides and/or waters of hydration. Thus, a "metal oxide" refers qualitatively to compositions wherein an elemental analysis reveals the presence of the relevant metal (in one or more valence states) and oxygen. For example, an exemplary porous support disclosed herein is a zirconia having formula $ZrO_2(OH)_x$. As is understood by those of skill in the art, the amount of oxygen measured in such an analysis will depend on a number of factors such as the valence state of the metal, for example a Group IVB or Group VIB metal, moisture content, and the like. For convenience, the metal oxides and porous supports can be referred to herein using formulas such as $XO_w/YO_z$ wherein, for example, X is a Group IVB metal such as zirconium, and Y is a Group VIB metal such as molybdenum or tungsten. It will be appreciated, however, that this notation is for convenience, and one or both the metal oxides as represented by $XO_w$ and $YO_z$ may comprise the corresponding hydroxides and/or contain waters of hydration. Thus, the heterogeneous catalysts described herein are not subject to a single specific formula for every embodiment.

Where the heterogeneous catalyst comprises a metal oxide in combination with a porous support, the metal oxide comprises molybdenum, tungsten, or a combination of metals comprising at least one of molybdenum and tungsten. Tungsten-containing oxide materials can be represented by $WO_x$, which includes $WO_3$ or $W_2O_6$. Molybdenum-containing oxide materials can be represented by $MoO_x$, which includes $MoO_3$ or $Mo_2O_6$. Other species, for example other metals can be present, provided that such species do not significantly adversely affect the use of the heterogeneous catalyst as described herein Where the heterogeneous catalyst comprises a metal oxide in combination with a porous support, various porous materials can be used as the support. Such materials included, for example, zirconium oxide (zirconia, $ZrO_2$), titanium oxide (titania, $TiO_2$ (anatase or rutile)), a lanthanide series metal oxide such as cerium oxide (ceria, $CeO_2$), aluminosilicates, silica ($SiO_2$), aluminum oxide (alumina, $Al_2O_3$ (acidic or neutral)), zinc oxide, magnesium oxide, niobium oxide, tin oxide, and combinations comprising at least one or more of the foregoing materials. Aluminosilicates, for example, can include various zeolites such as the SBA series of zeolites, such as SBA-11, SBA-12, and SBA-15. Other exemplary types of zeolites include mordenite, ZSM-5, L-zeolite, faujasite, ferrierite, and chabazite.

In one specific embodiment, the porous support is silica, cerium oxide, zirconium oxide, or cerium oxide-zirconium oxide. Tungsten oxide in combination with a zirconium oxide porous support is sometimes referred to as tungstated zirconia, $WO_x/ZrO_2$, and tungsten oxide in combination with a cerium oxide porous support is sometimes referred to as tungstated ceria, $WO_x/CeO_2$. In a specific embodiment, the heterogeneous catalyst is tungsten oxide in combination with zirconium oxide, tungsten oxide in combination with cerium oxide, tungsten oxide in combination with zirconium oxide-cerium oxide, or molybdenum oxide in combination with silicon oxide.

When the heterogeneous catalyst is a sulfated porous Group IVB metal oxide, a lanthanide series metal oxide, or a combination comprising at least one of the foregoing oxides, the metal oxide acts as a support. Catalysts of this type include sulfated zirconium oxide, sulfated cerium oxide, and combinations comprising at least one of the foregoing.

In either embodiment, the porous support can be a microporous or a mesoporous material. Mesoporous supports have a pore size of greater than or equal to about 10 to about 100 angstroms, and the microporous supports have a pore size of less than or equal to about 10 angstroms, as determined by BET measurements. The heterogeneous catalyst has a surface area of 10 to 600 $m^2/g$, specifically 20 to 200 $m^2/g$ measured in accordance with the BET method. The surface density of the tungsten or molybdenum (or both) in the heterogeneous catalyst is 2 to 30, specifically 3 to 12, atoms per amount nanometer square area, as determined according to the method of A Bordoloi et al, *Journal of Molecular Catalysis A; Chemical* 247 (2006) 58-64, page 60.

The heterogeneous catalysts can be made by a variety of methods. In an embodiment, the heterogeneous catalyst is manufactured by contacting (e.g., impregnating) a precursor of the porous support with a metal oxide precursor or sulfate anion precursor; and calcining the combined precursors. Other species, for example other metals, can be present during the reactions, provided that such species do not significantly adversely affect the use of the heterogeneous catalyst as described herein.

The precursor for the porous support comprises the metal oxide itself, a metal oxyhydroxide thereof, a metal hydroxide thereof, or a combination comprising at least one of the foregoing. One precursor of tungsten or molybdenum oxide is the corresponding oxyanions. Thus, in an embodiment, the heterogeneous catalyst comprises the reaction product of an oxyanion of molybdenum, an oxyanion of tungsten, or a combination of an oxyanion of molybdenum and oxyanion of tungsten with a porous support precursor. For example, ammonium metatungstate $(NH_4)_6H_2W_{12}O_{40}\cdot xH_2O$ (also known as AMT, wherein the molecular weight of the anhydrous portion, is 2956 Daltons) is commercially available in the form of highly soluble hydrated crystals, which can be used in powder form as a source of water-soluble tungsten. At room temperature, aqueous solutions can be saturated up to 70% by weight of contained WO$_3$. The porous support, such as a hydroxide of zirconium, is contacted with AMT, then water removed by drying and calcination, as described further in the examples below.

The amount of metal oxide or sulfate anions in the heterogeneous catalyst varies, depending on the type of metal oxide, the type of support, the desired activity of the heterogeneous catalyst, and like considerations. For example, the total amount of metal oxide is 5 to 30 weight percent (wt. %), specifically 10 to 20 wt. %, based on the weight of the support.

The amount of the heterogeneous catalyst used in the reaction varies, depending on the type of heterogeneous catalyst, its activity, the desired time for the reaction, and like considerations. In general, the amount of heterogeneous catalyst is 10 to 30 wt. %, specifically 12 to 25 wt. %, more specifically 15 to 20 wt. %, based on the total weight of phenolic compound and the phthalimide compound.

If necessary, a promoter can be present. Exemplary promoters include chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, and combinations comprising at least one of the foregoing promoters. Specific promoters include chlorosulphonic acid, methanesulphonic acid, dodecylbenzenesulphonic acid, triflic acid, boron trifluoride, p-toluene sulphonyl chloride, and combinations comprising at least one of the foregoing. In an embodiment, the promoter is chlorosulphonic acid.

The promoter is present in an amount of up to 6 mol %, more specifically, 0.05 to 5 mol %, based on the moles of phthalic anhydride. Specifically, chlorosulphonic acid is present in an amount of 0.05 to 0.5 molar equivalents, more specifically 0.1 to 0.3 molar equivalents, with respect to the phthalimide compound.

In an embodiment, the catalyst is an acid catalyst. Examples of acid catalysts that can be used include, but are not limited to, mineral acids such as hydrochloric acid (HCl), sulfuric acid, nitric acid, and phosphoric acid; weak inorganic acids such as boric acid, organic sulfonic acids such as methanesulfonic acid, Lewis acids such as stannic chloride, ferric chloride, aluminum chloride, and zinc chloride; sulfated zirconia; or combinations of two or more of the foregoing acid catalysts. Suitable acid catalysts also include amine salts of the above mineral acids. Examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. In a specific embodiment, the catalyst used is aluminum chloride. It can be used in an amount of 1 to 10 molar equivalents, 2 to 8 molar equivalents, and 4 to 6 molar equivalents based on the molar of phthalimide of formula (2).

The produced 2-hydrocarbyl-3,3-bis(hydroxyaryl)phthalimidine compositions can comprise 2-phenyl-3,3-bis(4-hydroxyphenyl)phthalimidine of formula (6) and 2-phenyl-3-(4-hydroxyphenyl)-3-(2-hydroxyphenyl)phthalimidine of formula (7) having a molar ratio of 95:5 to 5:95.

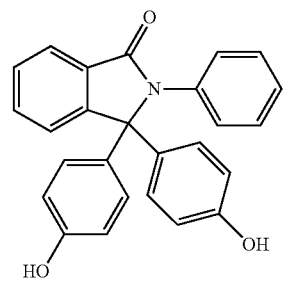

(6)

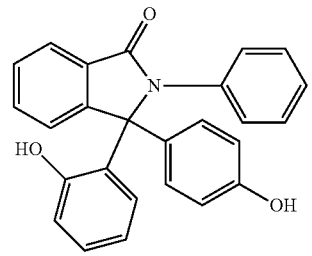

(7)

Solvent is optional for the reaction. In some embodiments, the reaction is carried out in the absence of any solvent. In the absence of solvent, the produced 2-hydrocarbyl-3,3-bis(hydroxyaryl)phthalimidines composition comprises 2-phenyl-3,3-bis(4-hydroxyphenyl)phthalimidine compound of formula (6) and 2-phenyl-3-(4-hydroxyphenyl)-3-(2-hydroxyphenyl)phthalimidine compound of formula (7) having a molar ratio of 95:5 to 90:10, for example 93 to 7.

It was surprisingly found that when different solvents are used, the ratio of the compound of formula (6) and the compound of formula (7) may be affected. For example, when 1,1,2,2-tetrachloroethane or chlorobenzene is used as the solvent, the produced 2-hydrocarbyl-3,3-bis(hydroxyaryl)phthalimidines composition comprises a compound of formula (6) and a compound of formula (7) having a molar ratio of 5:95 to 20:80, for example, 15:85 or 14:86. When o-dichlorobenzene is used as the solvent, the produced 2-hydrocarbyl-3,3-bis(hydroxyaryl)phthalimidines composition comprises a compound of formula (6) and a compound of formula (7) having a molar ratio of 95:5 to 80:20, for example, 90:10, 86:14, or 85:15. If excess phenol is used, the produced 2-hydrocarbyl-3,3-bis(hydroxyaryl)phthalimidines can be crystallized as adduct with excess phenol of formula (3).

If desired, the compound of formula (7) can be converted to the compound of formula (6) by acid catalyzed isomerization in the presence of excess phenol. The acid catalyst can be a protonic acid, a Lewis acid, or an acid ion exchange resin. For example, the acid catalyst can be a catalyst described in U.S. Pat. No. 4,822,923 and RE34,626 for the isomerization of bisphenols.

The conditions for the reaction vary, depending on the particular phenolic compound, phthalimide compound, and catalyst used. In an embodiment, the reaction is conducted at an elevated temperature, for example, a temperature of 100° C. to 200° C., specifically 120 to 180° C., more specifically 140 to 160° C., for a reaction time of 10 to 100 hours, 20 to 70 hours, 30 to 60 hours, less than 30 hours, less than 28 hours and less than 24 hours. The progress of the reaction can be followed by numerous analytical techniques such as gas chromatography or high-pressure liquid chromatography (HPLC).

The crude product can be cooled and quenched by mixing with an acid and an organic solvent. The acid can be a mineral acid, hydrochloride acid, or a combination thereof. The organic solvent can be at least one of diethyl ether, chloroform, methylene chloride, benzene, toluene, pentane, hexane, cyclohexane, and 1,2-dichloromethane. In a specific embodiment, the solvent comprises hexane. After quenching, solids precipitate, which can be filtered and dried to provide 2-hydrocarbyl-3,3-bis(hydroxyaryl)phthalimidine composition.

The phthalimide of formula (2) can be prepared by reacting an anhydride of formula (4) with an amine of formula (5)

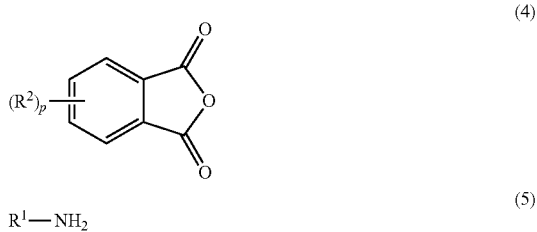

to provide the phthalimide, wherein $R^1$, $R^2$, p and q are the same as described herein above.

The 2-hydrocarbyl-3,3-bis(hydroxyaryl)phthalimidine composition prepared according to the method described herein comprises less than 100 ppm of an amino phenol of formula (8)

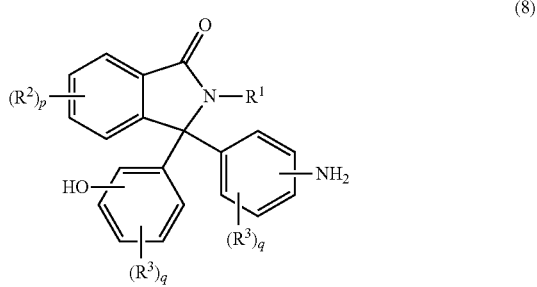

wherein $R^1$, $R^2$, $R^3$, p and q are the same as described herein above. In a specific embodiment, the 2-hydrocarbyl-3,3-bis(hydroxyaryl)phthalimidine composition is free of an amino phenol of formula (8) even without charcoal purification. Accordingly, the method avoids the use of activated carbon thus reducing material waste.

In some embodiments, 2-hydrocarbyl-3,3-bis(hydroxyaryl)phthalimidine is obtained at a purity of at greater than or equal to 80 wt. %, specifically 90 to 99 wt. %, more specifically 94 to 97 wt. %, based on the total weight of the crude 2-hydrocarbyl-3,3-bis(hydroxyaryl)phthalimidine. The 2-hydrocarbyl-3,3-bis(hydroxyaryl)phthalimidine compound is obtained in a yield of greater than or equal to 70 mol %, specifically greater than or equal to 80 mol %, based on the moles of phthalimide. In an embodiment, the 2-hydrocarbyl-3,3-bis(hydroxyaryl)phthalimidine compound is obtained both at a purity of greater than 80 wt. %, specifically 90 to 99 wt. %, more specifically 94 to 97 wt. %, based on the total weight of crude 2-hydrocarbyl-3,3-bis(hydroxyaryl)phthalimidine, and in a yield of greater than or equal to 70 mol %, specifically greater than or equal to 80 mol %, based on the moles of phthalimide compound.

To obtain a purified (>99.5%) phthalimidine compound, at least one trituration is required on the crude product. Trituration can be conducted using aqueous methanol, in particular a solution comprising 5% to 20% by volume water and 80 to 95% by volume methanol. In some embodiments, trituration can be conducted at an elevated temperature that is below the boiling point of the aqueous methanol, for example 45° C. to 90° C., more specifically 50° C. to 80° C. for 10 minutes to 5 hours, or 30 minutes to 3 hours, or 1 to 3 hours. Alternatively or in combination, trituration can be conducted using 1,2-dichloroethane or a composition comprising 10% to 30% by volume toluene and 70 to 90% by volume methanol. When 1,2-dichloroethane is used, trituration can be conducted at 40° C. to 100° C. When a methanol and toluene blend is used, trituration can be conducted at 40° C.-70° C. or 50-60° C. In necessary, activated carbon can be used to further purify the crude product.

The 2-hydrocarbyl-3,3-bis(hydroxyaryl)phthalimidine of formula (1) can be used to manufacture polycarbonate. The method can comprise polymerizing the 2-hydrocarbyl-3,3-bis(hydroxyaryl)phthalimidine of formula (1) and optionally a dihydroxy aromatic compound different from the 2-hydrocarbyl-3,3-bis(hydroxyaryl)phthalimidine of formula (1) thereby making the polycarbonate.

Some illustrative examples of specific dihydroxy aromatic compounds different from the 2-hydrocarbyl-3,3-bis(hydroxyaryl)phthalimidine of formula (1) are those described in in WO 2013/175448 A1, US 2014/0295363, and WO 2014072923. The aromatic dihydroxy compound can be a bisphenol. Specific examples of bisphenol compounds include 1,1-bis(4-hydroxyphenyl) methane, 1,1-bis(4-hydroxyphenyl) ethane, 2,2-bis(4-hydroxyphenyl) propane (hereinafter "bisphenol-A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, and 1,1-bis(4-hydroxy-3-methylphenyl)cyclohexane (DMBPC). Combinations comprising at least one of the foregoing dihydroxy compounds can also be used. In a specific embodiment, the optional dihydroxy aromatic compound is bisphenol A.

Polycarbonates can be manufactured by processes such as interfacial polymerization and melt polymerization. Such processes are known, and are described, for example, in WO 2013/175448 A1 and WO 2014/072923 A1. An end-capping agent (also referred to as a chain stopper agent or chain terminating agent) can be included during polymerization to provide end groups, for example monocyclic phenols such as phenol, p-cyanophenol, and $C_1$-$C_{22}$ alkyl-substituted phenols such as p-cumyl-phenol, resorcinol monobenzoate, and p- and tertiary-butyl phenol, monoethers of diphenols, such as p-methoxyphenol, monoesters of diphenols such as resorcinol monobenzoate, functionalized chlorides of aliphatic monocarboxylic acids, such as acryloyl chloride and methacryoyl chloride, and mono-chloroformates such as phenyl chloroformate, alkyl-substituted phenyl chloroformates, p-cumyl phenyl chloroformate, and toluene chloroformate. Combinations of different end groups can be used. Branched polycarbonate blocks can be prepared by adding a branching agent during polymerization, for example trimellitic acid, trimellitic anhydride, trimellitic trichloride, tris-p-hydroxyphenylethane, isatin-bis-phenol, tris-phenol TC (1,3,5-tris ((p-hydroxyphenyl)isopropyl)benzene), tris-phenol PA (4(4

(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of 0.05 to 2.0 wt. %. Combinations comprising linear polycarbonates and branched polycarbonates can be used.

Polycarbonates manufactured and purified as described herein are suitable for use in a wide variety of compositions and applications as is known in the art. Thus, an additive composition can be added to the purified polycarbonate form a polycarbonate composition. The additive composition can one or more additives selected to achieve a desired property, with the proviso that the additive(s) are also selected so as to not significantly adversely affect a desired property of the thermoplastic composition. The additive composition or individual additives can be mixed at a suitable time during the mixing of the components for forming the composition. The additive can be soluble and/or non-soluble in polycarbonate.

The additive composition can include an impact modifier, flow modifier, filler (e.g., a particulate polytetrafluoroethylene (PTFE), glass, carbon, mineral, or metal), reinforcing agent (e.g., glass fibers), antioxidant, heat stabilizer, light stabilizer, ultraviolet (UV) light stabilizer, UV absorbing additive, plasticizer, lubricant, release agent (such as a mold release agent), antistatic agent, anti-fog agent, antimicrobial agent, colorant (e.g., a dye or pigment), surface effect additive, radiation stabilizer, flame retardant, anti-drip agent (e.g., a PTFE-encapsulated styrene-acrylonitrile copolymer (TSAN)), or a combination comprising one or more of the foregoing. For example, a combination of a heat stabilizer, mold release agent, and ultraviolet light stabilizer can be used. In general, the additives are used in the amounts generally known to be effective. For example, the total amount of the additive composition (other than any impact modifier, filler, or reinforcing agent) can be 0.001 to 10.0 wt. %, or 0.01 to 5 wt. %, each based on the total weight of the polymer in the composition.

Set forth below are some embodiments of the methods for the manufacture of 2-hydrocarbyl-3,3-bis(hydroxyaryl) phthalimidine compositions and polycarbonate compositions.

In an embodiment, a method for the manufacture of a 2-hydrocarbyl-3,3-bis(hydroxyaryl)phthalimidine composition comprises: reacting a phthalimide of formula (2) with a phenol of formula (3) in the presence of a catalyst and optionally a solvent at an elevated temperature to form the 2-hydrocarbyl-3,3-bis(hydroxyaryl)phthalimidine composition, wherein the 2-hydrocarbyl-3,3-bis(hydroxyaryl)phthalimidine composition comprises a 2-hydrocarbyl-3,3-bis(hydroxyaryl)phthalimidine of formula (1), wherein in formulas (1), (2) and (3), $R^1$ is hydrogen, $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are independently 0 to 4.

In another embodiment, a method for the manufacture of a polycarbonate comprises: reacting a phthalimide of formula (2) with a phenol of formula (3) in the presence of a catalyst and optionally a solvent at an elevated temperature to form a 2-hydrocarbyl-3,3-bis(hydroxyaryl)phthalimidine composition comprising a 2-hydrocarbyl-3,3-bis(hydroxyaryl)phthalimidine of formula (1), and polymerizing the 2-hydrocarbyl-3,3-bis(hydroxyaryl)phthalimidine of formula (1) and optionally a dihydroxy aromatic compound different from the 2-hydrocarbyl-3,3-bis(hydroxyaryl) phthalimidine of formula (1) such as bisphenol A to form the polycarbonate, wherein in formulas (1), (2) and (3), $R^1$ is hydrogen, $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are independently 0 to 4.

In specific embodiments of the foregoing methods for the manufacture of 2-hydrocarbyl-3,3-bis(hydroxyaryl)phthalimidine compositions and polycarbonate compositions, one or more of the following conditions can apply: (a) the methods further comprises: reacting an anhydride of formula (4) with an amine of formula (5) to provide the phthalimide of formula (2), wherein $R^1$ is hydrogen, $C_{1-6}$ alkyl, $C_{1-6}$ alkoxy, or phenyl optionally substituted with 1 to 5 $C_{1-6}$ alkyls, each occurrence of $R^2$ is independently a $C_{1-6}$ alkyl, and p is 0 to 4; (b) $R^1$ is phenyl; (c) the 2-hydrocarbyl-3,3-bis(hydroxyaryl)phthalimidine composition comprises a 2-phenyl-3,3-bis(4-hydroxyphenyl)phthalimidine of formula (6), a 2-phenyl-3-(4-hydroxyphenyl)-3-(2-hydroxyphenyl)phthalimidine of formula (7), or a combination thereof; (c) the molar ratio of the 2-phenyl-3,3-bis(4-hydroxyphenyl)phthalimidine of formula (6) to the 2-phenyl-3-(4-hydroxyphenyl)-3-(2-hydroxyphenyl)phthalimidine of formula (7) is 95:5 to 5:95; (d) the solvent is 1,2-dichlorobenzene; and the 2-hydrocarbyl-3,3-bis(hydroxyaryl) phthalimidine composition comprises a 2-phenyl-3,3-bis(4-hydroxyphenyl)phthalimidine of formula (6), and a 2-phenyl-3-(4-hydroxyphenyl)-3-(2-hydroxyphenyl)phthalimidine (7), and having a molar ratio of formula (6):(7) of 95:5 to 80:20; (e) the solvent is 1,1,2,2-tetrachloroethane; and the 2-hydrocarbyl-3,3-bis(hydroxyaryl)phthalimidine composition comprises a 2-phenyl-3,3-bis(4-hydroxyphenyl)phthalimidine of formula (6) and a 2-phenyl-3-(4-hydroxyphenyl)-3-(2-hydroxyphenyl)phthalimidine (7), and having a molar ratio of formula (6):(7) of 5:95 to 20:80; (f) the methods further comprise converting the 2-phenyl-3-(4-hydroxyphenyl)-3-(2-hydroxyphenyl)phthalimidine of formula (7) to the 2-phenyl-3,3-bis(4-hydroxyphenyl)phthalimidine of formula (6); (g) $R^1$ is methyl; (h) the catalyst used to form the 2-hydrocarbyl-3,3-bis(hydroxyaryl)phthalimidine of formula (1) is an acid catalyst; (i) the catalyst used to form the 2-hydrocarbyl-3,3-bis(hydroxyaryl)phthalimidine of formula (1) is $AlCl_3$; (j) the molar ratio of the phenol of formula (3) to the phthalimide of formula (2) is greater than 2; (k) the molar ratio of the phenol of formula (3) to the phthalimide of formula (2) is 2 to 10, preferably 3 to 6; (l) the elevated temperature is 100° C. to 200° C.; (m) the 2-hydrocarbyl-3,3-bis(hydroxyaryl)phthalimidine composition is manufactured in less than 30 hours; (n) the methods further comprises cooling a crude product of the phthalimide of formula (2) and the phenol of formula (3) and quenching the cooled crude product by stirring with an acid and an organic solvent; (o) the acid is a mineral acid; (p) the acid comprises hydrochloric acid; (q) the organic solvent is at least one of diethyl ether, chloroform, methylene chloride, benzene, toluene, pentane, hexane, cyclohexane, and 1,2-dichloroethane; (r) the organic solvent is hexane; (s) the methods further comprise filtering and drying the quenched crude product to provide the 2-hydrocarbyl-3,3-bis(hydroxyaryl)phthalimidine composition; (t) the methods further comprise purifying the crude product by trituration; (u) the methods further comprise purifying the crude product using activated carbon; (v) 2-hydrocarbyl-3,3-bis(hydroxyaryl) phthalimidine composition comprises less than 100 ppm of an amino phenol, 2-aryl-3-(aminoaryl-3-(hydroxyaryl) phthalimidine of formula (8) and less than 100 ppm of 2-phenyl-3-(4-hydroxyphenyl)-3-(2-hydroxyphenyl)phthalimidine of formula (7); (w) the 2-hydrocarbyl-3,3-bis(hydroxyaryl)phthalimidine composition is free of an amino phenol of formula (8) and 2-phenyl-3-(4-hydroxyphenyl)-3-(2-hydroxyphenyl)phthalimidine of formula (7).

In another embodiment, disclosed is a 2-hydrocarbyl-3,3-bis(hydroxyaryl)phthalimidine composition manufactured by a method of any one or more of the foregoing embodiments.

A polycarbonate manufactured by a method of any one or more of the foregoing embodiments is also disclosed.

The method of the manufacture of 2-hydrocarbyl-3,3-bis(hydroxyaryl)phthalimidines is further illustrated by the following non-limiting examples.

EXAMPLES

Example 1. Synthesis of N-phenylphthalimide (NPP)

In a 500 ml three necked round bottom flask connected with a dean stark apparatus and an overhead stirrer, 50 grams of phthalic anhydride, 31.5 grams of aniline, and 250 ml of oDCB (1,2-dichlorobenzene) were added; and the reaction mixture was heated at 180-190° C. for 5 h to remove the water. After this, the reaction mixture was brought to room temperature and major part of oDCB was decanted. Methanol was added to the residue and the resulting mixture was heated at 65° C. for 30 min. The precipitate was then filtered, washed with small aliquots of methanol and dried to obtain NPP as colorless solid in quantitative yield. Purity by HPLC area was 99.7%.

Example 2. Synthesis of PPPBP Containing o,p'-PPPBP as Major Product

In a 250 ml two necked round bottom flask fitted with a reflux condenser (nitrogen blanket), 2 grams of NPP, 6 grams of aluminum chloride, 8.5 g of phenol, and 20 ml of 1,1,2,2-tetrachloroethane were added and the reaction mixture was heated at 155° C. for 16 hours. Then the reaction mixture was brought to room temperature and 100 ml of 10% aqueous HCl and 20 mL of hexane were added. The resultant mixture was stirred for 30 min at room temperature. The formed precipitate was filtered and washed thoroughly with water until acid free. The washed precipitate was dried in an oven to provide the product. Crude yield: about 86% (dry weight), HPLC area % result: p,p'-PPPBP=9%, o,p'-PPPBP=82%, and N-phenylphthalimide=0.6%.

Example 3. Synthesis of PPPBP Containing p,p'-PPPBP as Major Product

A. In a 250 ml two necked round bottom flask fitted with a dean stark, 2 grams of NPP, 6 grams of aluminum chloride, 4.3 g of phenol and 20 ml of 1,2-dichlorobenzene were added and the reaction mixture was heated at 150° C. for 18 hours. Then the reaction mixture was brought to room temperature, and 100 ml of 10% aqueous HCl and 20 mL of hexane were added. The resultant mixture was stirred for 30 min at room temperature. The formed precipitate was filtered and washed thoroughly with water until acid free. The washed product was dried in an oven to provide the product. Crude yield: ~91% (dry weight), HPLC wt. % result: p,p'-PPPBP=90%, o,p'-PPPBP=3.1%, and N-phenylphthalimide=2.8%.

B. In a 1000 ml two necked round bottom flask fitted with a dean stark, 10 grams (0.045 moles) of NPP, 30 grams (0.22 moles) of aluminum chloride, 12.6 grams (0.13 moles) of phenol and 75 ml of 1,2-dichlorobenzene were added and the reaction mixture was heated at 160° C. for 15-20 hours. Then the reaction mixture was brought to 55-60° C., followed by addition of 200 ml of water and 100 ml of hexane. The resultant mixture was stirred for 60 min at that temperature, then brought down to room temperature. The formed precipitate was filtered and washed first with hexane and then thoroughly with water until acid free. The product was dried in oven. Crude yield: 94% (dry weight), HPLC purity: p,p'-PPPBP (area %)=91%, o,p-PPPBP (area %)=2%, and N-phenylphthalimide (area %)=1.9%.

Example 4-8

Synthesis of PPPBP—Effect of Reaction Temperature and Catalyst Loading Level Example 3 was repeated using 2 g NPP and 5 molar equivalents of phenol except that the amount of $AlCl_3$, oDCB, reaction temperature and reaction time were varied as shown in Table 1. The results are summarized in Table 1.

TABLE 1

| | $AlCl_3$ | oDCB | Temp | Time | PPPBP | | o,p'-PPPBP | NPP |
|---|---|---|---|---|---|---|---|---|
| | (mol eq) | (mL) | (° C.) | (h) | Wt. % | Area % | Area % | Area % |
| Ex4 | 5 | 20 | 120 | 65 | 82.5 | 74 | 21 | 2 |
| Ex5 | 5 | 20 | 100 | 85 | | 32 | 46 | 17 |
| Ex6 | 5 | 20 | 150 | 18 | | | | |
| Ex7 | 2.5 | 10 | 100 | 85 | | 20 | | 78 |
| Ex8 | 2.5 | 10 | 150 | 18 | | | | |

Examples 9-12. Synthesis of PPPBP—Effect of Phenolic Compound Equivalent

Example 3 was repeated using 2 g of NPP and 5 molar equivalents of $AlCl_3$ at 120° C. reaction temperature except the amount of phenol was varied as shown in Table 2. The results of examples 4 and 9-12 are summarized in Table 2.

TABLE 2

| | PhOH | Time | PPPBP | | o,p'-PPPBP | NPP |
|---|---|---|---|---|---|---|
| | (mol eq) | (h) | Wt. % | Area % | Area % | Area % |
| Ex9 | 10 | 40 | 86.5 | 80 | 13 | 1 |
| Ex4 | 5 | 65 | 82.5 | 74 | 21 | 2 |
| Ex10 | 2.5 | 40 | | 7 | — | 92 |
| Ex11 | 3 | 20 | | 89 | 3 | 2 |
| Ex12 | 2.1 | 20 | | 13 | 1.1 | 68 |

Example 13. Synthesis of PPPBP—Effect of AlCl₃ Equivalents

Example 3 was repeated using 2 g of NPP and 10 molar equivalents of phenol, and AlCl₃ in an amount as shown in Table 3. The results of example 13 as well as examples 5-9 are summarized in Table 3.

TABLE 3

|  | AlCl₃ (mol eq) | oDCB (mL) | Temp (° C.) | Time (h) | PPPBP Wt. % | PPPBP Area % | o,p'-PPPBP Area % | NPP Area % |
|---|---|---|---|---|---|---|---|---|
| Ex9 | 5 | 20 | 120 | 40 | 86.5 | 80 | 13 | 1 |
| Ex13 | 1 | 20 | 120 | 43 |  | 22 | 7 | 70 |
| Ex5 | 5 | 20 | 100 | 85 |  | 32 | 46 | 17 |
| Ex7 | 2.5 | 10 | 100 | 85 |  | 20 | — | 78 |
| Ex6 | 5 | 20 | 150 | 18 |  |  |  |  |
| Ex8 | 2.5 | 10 | 150 | 18 |  |  |  |  |

Examples 14-20. Synthesis of PPPBP—Effect of Phenol and AlCl₃ Equivalents

Example 3 was repeated using 2 g of NPP and molar equivalents of phenol, and AlCl₃ in an amount as shown in Table 4. The results are summarized in Table 4.

TABLE 4

|  | PhOH (mol eq) | AlCl3 (mol eq) | oDCB (mL) | Temp (° C.) | Time (h) | PPPBP Area % | o,p'-PPPBP Area % | NPP Area % |
|---|---|---|---|---|---|---|---|---|
| Ex 14 | 3 | 5 | 20 | 160 | 20 | 89 | 3 | 2 |
| Ex 15 | 3 | 4 | 20 | 160 | 20 | 85 | 2 | 7 |
| Ex 16 | 3 | 3 | 20 | 160 | 20 | 76 | 8 | 7 |
| Ex 17 | 2.5 | 3 | 20 | 160 | 20 | 78 | 5.6 | 10 |
| Ex 18 | 2.5 | 3.5 | 20 | 160 | 24 | 84 | 2 | 8 |
| Ex 19 | 2.5 | 4 | 20 | 160 | 24 | 83 | 1.5 | 9 |
| Ex 20 | 2.1 | 4 | 20 | 160 | 24 | 72 | 1 | 18 |

Examples 21-25. Synthesis of PPPBP—Comparison of Using Different Solvents

Example 3 was repeated using 2 g of NPP and 10 molar equivalents of phenol, and 5 molar equivalents of AlCl₃ in the presence of a solvent as shown in Table 5. The results of examples 12-16 as well as example 9 are summarized in Table 5.

TABLE 5

|  | Solvent | Temp (° C.) | Time (h) | PPPBP Area % | o,p'-PPPBP Area % | NPP Area % |
|---|---|---|---|---|---|---|
| Ex21 | Ethylene glycol | 145 | 72 | 23 | — | 18 |
| Ex22 | PEG 200 | 145 | 72 | — | — | 100 |
| Ex23 | 1,1,2,2-tetrachloroethane | 120 | 40 | 34 | 61 | 0 |
| Ex9 | oDCB | 120 | 40 | 80 | 13 | 1 |
| Ex24 | Chlorobenzene | 120 | 187 | 19 | 77 | — |
| Ex25 | Nitrobenzene | 120 | 18 | 18 | * | * |

* many peaks.

Example 26. Purification of PPPBP

The crude PPPBP (10 g) obtained from Example 3B was suspended in 30 ml of 1,2-dichloroethane and the resultant mixture was heated to 90° C. for 2 h. The mixture was then cooled to 50° C. and the resultant slurry was filtered, washed with 10 ml of hot 1,2-dichloroethane and dried.

The solid thus obtained along with 0.5 g of urea was dissolved in 130 ml of methanol:toluene (7:2) solvent mixture under heat (50-60° C.). Activated charcoal (1 g) was added to the solution. The resultant mixture was heated at 80° C. for 1 h. Charcoal was filtered and washed with 20-30 ml of hot methanol. The filtrate obtained was concentrated to 3-4 vol % based on the volume of the crude and the resultant mixture was stirred at room temperature for about an hour to gradually precipitate the product. Complete crystallization/precipitation was ensured by stirring the slurry at 0° C. for about ½ h. The precipitated product was filtered and washed with ice cold methanol (1 vol % based on the volume of the crude) and dried.

The product thus obtained was suspended in methanol:water (90:10) solvent mixture and the resultant mixture was heated to 80-85° C. for 1 h. The slurry was then cooled to 10° C. and was held at that temperature for 1 h. The solid was then filtered, washed with ice cold methanol:water mixture and dried. The solid thus obtained was refluxed with water for 1 h, filtered, and dried. The procedure described in this paragraph was repeated. The resultant product obtained had a purity of 99.1% (HPLC area %).

The product with 99.1 (HPLC area %) purity was dissolved in methanol:toluene (7:2) solvent mixture under heat (50-60° C.), then filtered to remove any suspended particles, concentrated, and stirred at room temperature for 1 h to gradually precipitate the product. Complete crystallization/precipitation was ensured by stirring the slurry at 0° C. for about ½ h. The precipitated product was filtered and washed with ice cold methanol and dried in oven for 8 hrs at 105° C.

The product thus obtained was off-white in color with purity ~99.9% (HPLC wt %), o,p-PPPBP (HPLC wt %)=14 ppm, and N-phenylphthalimide (HPLC wt. %)=8 ppm.

The singular forms "a," "an," and "the" include plural referents unless the context clearly dictates otherwise. "Or" means "and/or." The endpoints of all ranges directed to the same component or property are inclusive and independently combinable. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

As used herein, a "combination" is inclusive of blends, mixtures, alloys, reaction products, and the like. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl" and "hydrocarbon" refer broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms; "aryl" refers to an aromatic monovalent group containing only carbon in the aromatic ring or rings; "arylene" refers to an aromatic divalent group containing only carbon in the aromatic ring or rings; "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylenearyl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for the manufacture of a 2-hydrocarbyl-3,3-bis(hydroxyaryl)phthalimidine composition, the method comprising reacting a phthalimide of formula (2) with a phenol of formula (3)

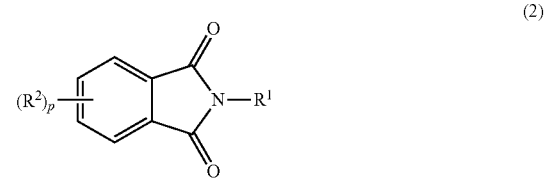

in the presence of a catalyst and optionally a solvent at an elevated temperature to form the 2-hydrocarbyl-3,3-bis(hydroxyaryl)phthalimidine composition, wherein the 2-hydrocarbyl-3,3-bis(hydroxyaryl)phthalimidine composition comprises a 2-hydrocarbyl-3,3-bis(hydroxyaryl)phthalimidine of formula (1)

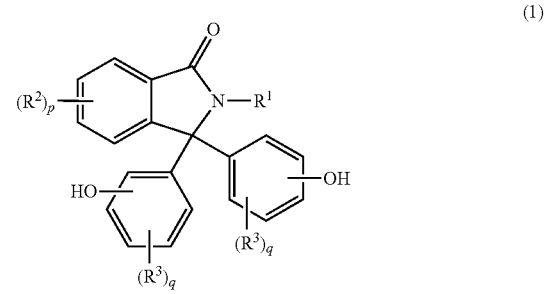

wherein in formulas (1), (2) and (3), $R^1$ is $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are independently 0 to 4.

2. A method for the manufacture of a polycarbonate comprising reacting a phthalimide of formula (2) with a phenol of formula (3)

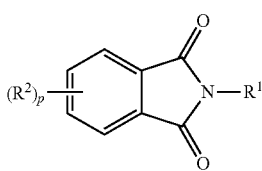

(2)

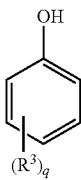

(3)

in the presence of a catalyst and optionally a solvent at an elevated temperature to form a 2-hydrocarbyl-3,3-bis(hydroxyaryl)phthalimidine composition comprising a 2-hydrocarbyl-3,3-bis(hydroxyaryl)phthalimidine of formula (1)

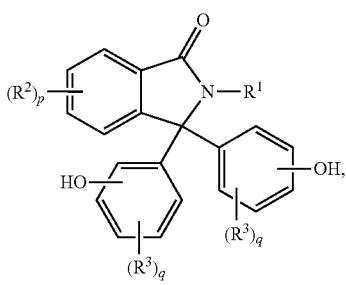

(1)

and
polymerizing the 2-hydrocarbyl-3,3-bis(hydroxyaryl) phthalimidine of formula (1) and optionally a dihydroxy aromatic compound different from the 2-hydrocarbyl-3,3-bis(hydroxyaryl)phthalimidine of formula (1) to form the polycarbonate,
wherein in formulas (1), (2) and (3),
$R^1$ is $C_{1-6}$ alkyl, $C_{1-6}$ alkoxy, or phenyl optionally substituted with 1 to 5 $C_{1-6}$ alkyls,
each occurrence of $R^2$ and $R^3$ is independently a $C_{1-6}$ alkyl, and
p and q are independently 0 to 4.

3. The method of claim 1, further comprising reacting an anhydride of formula (4) with an amine of formula (5)

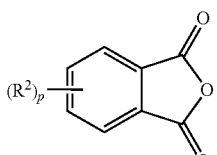

(4)

$R^1$—NH$_2$ (5)

to provide the phthalimide of formula (2), wherein
$R^1$ is $C_{1-6}$ alkyl, $C_{1-6}$ alkoxy, or phenyl optionally substituted with 1 to 5 $C_{1-6}$ alkyls,
each occurrence of $R^2$ is independently a $C_{1-6}$ alkyl, and
p is 0 to 4.

4. The method of claim 1, wherein $R^1$ is phenyl or methyl.

5. The method of claim 1, wherein the 2-hydrocarbyl-3,3-bis(hydroxyaryl)phthalimidine composition comprises a 2-phenyl-3,3-bis(4-hydroxyphenyl)phthalimidine of formula (6), a 2-phenyl-3-(4-hydroxyphenyl)-3-(2-hydroxyphenyl)phthalimidine of formula (7), or a combination thereof

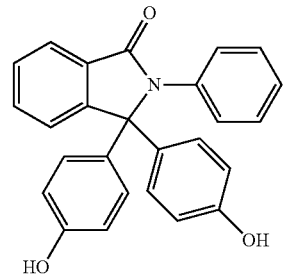

(6)

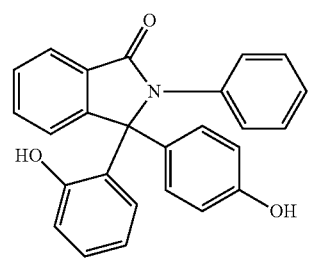

(7)

optionally wherein a molar ratio of the 2-phenyl-3,3-bis (4-hydroxyphenyl)phthalimidine of formula (6) to the 2-phenyl-3-(4-hydroxyphenyl)-3-(2-hydroxyphenyl) phthalimidine of formula (7) is 95:5 to 5:95.

6. The method of claim 1, wherein
the solvent is 1,2-dichlorobenzene; and
the 2-hydrocarbyl-3,3-bis(hydroxyaryl)phthalimidine composition comprises a 2-phenyl-3,3-bis(4-hydroxyphenyl)phthalimidine of formula (6) and a 2-phenyl-3-(4-hydroxyphenyl)-3-(2-hydroxyphenyl)phthalimidine (7)

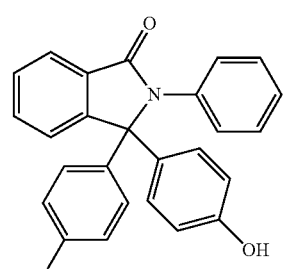

(6)

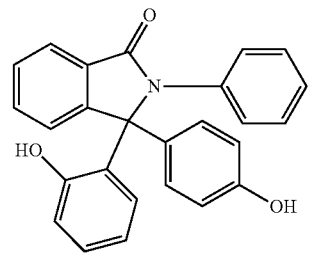

(7)

having a molar ratio of formula (6):(7) of 95:5 to 80:20.

7. The method of claim 1, wherein
the solvent is 1,1,2,2-tetrachloroethane; and
the 2-hydrocarbyl-3,3-bis(hydroxyaryl)phthalimidine composition comprises a 2-phenyl-3,3-bis(4-hydroxyphenyl)phthalimidine of formula (6) and a 2-phenyl-3-(4-hydroxyphenyl)-3-(2-hydroxyphenyl)phthalimidine (7)

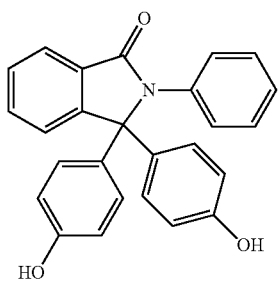

(6)

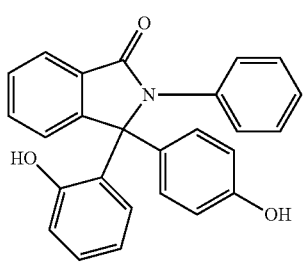

(7)

and having a molar ratio of formula (6):(7) of 5:95 to 20:80.

8. The method of claim 5, further comprising converting the 2-phenyl-3-(4-hydroxyphenyl)-3-(2-hydroxyphenyl)phthalimidine of formula (7) to the 2-phenyl-3,3-bis(4-hydroxyphenyl)phthalimidine of formula (6).

9. The method of claim 1, wherein the catalyst used to form the 2-hydrocarbyl-3,3-bis(hydroxyaryl)phthalimidine of formula (1) is an acid catalyst or $AlCl_3$.

10. The method of claim 1, wherein the molar ratio of the phenol of formula (3) to the phthalimide of formula (2) is greater than 2.

11. The method of claim 1, wherein the elevated temperature is 100° C. to 200° C.

12. The method of claim 1, wherein the method further comprises cooling a crude product of the phthalimide of formula (2) and the phenol of formula (3) and quenching the cooled crude product by stirring with an acid and an organic solvent.

13. The method of claim 12, wherein the acid is a mineral acid.

14. The method of claim 12, wherein the organic solvent is at least one of diethyl ether, chloroform, methylene chloride, benzene, toluene, pentane, hexane, cyclohexane, and 1,2-dichloroethane.

15. The method of claim 12, further comprising filtering and drying the quenched crude product to provide the 2-hydrocarbyl-3,3-bis(hydroxyaryl)phthalimidine composition.

16. The method of claim 15, further comprising purifying the crude product by trituration, purifying the crude product using activated carbon, or a combination comprising at least one of the foregoing.

17. The method of claim 1, wherein 2-hydrocarbyl-3,3-bis(hydroxyaryl)phthalimidine composition comprises less than 100 ppm of an amino phenol, 2-aryl-3-(aminoaryl-3-(hydroxyaryl)phthalimidine of formula (8) and less than 100 ppm of 2-phenyl-3-(4-hydroxyphenyl)-3-(2-hydroxyphenyl)phthalimidine of formula (7)

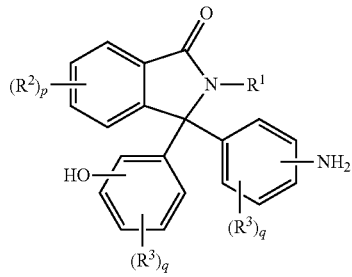

(8)

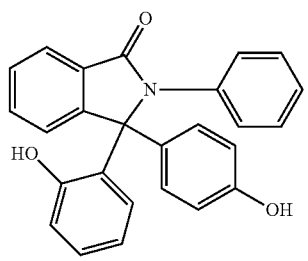

(7)

wherein
$R^1$ is $C_{1-6}$ alkyl, $C_{1-6}$ alkoxy, or phenyl optionally substituted with 1 to 5 $C_{1-6}$ alkyls,
each occurrence of $R^2$ and $R^3$ is independently a $C_{1-6}$ alkyl, and
p and q are each independently 0 to 4.

18. The method of claim 1, wherein the 2-hydrocarbyl-3,3-bis(hydroxyaryl)phthalimidine composition is free of an amino phenol of formula (8) and 2-phenyl-3-(4-hydroxyphenyl)-3-(2-hydroxyphenyl)phthalimidine of formula (7)

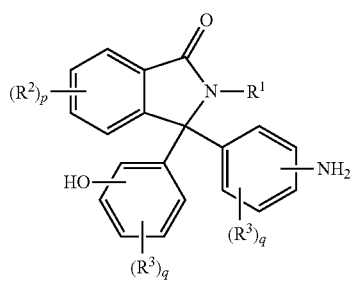

(8)

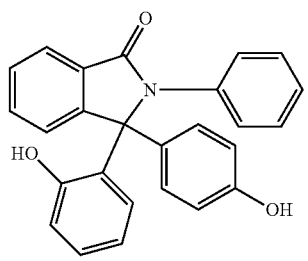

(7)

wherein
$R^1$ is $C_{1-6}$ alkyl, $C_{1-6}$ alkoxy, or phenyl optionally substituted with 1 to 5 $C_{1-6}$ alkyls, each occurrence of $R^2$ and $R^3$ is independently a $C_{1-6}$ alkyl, and p and q are independently 0 to 4.

19. A 2-hydrocarbyl-3,3-bis(hydroxyaryl)phthalimidine composition manufactured by a method of claim 1.

20. A polycarbonate manufactured by a method of claim 2.

21. The 2-hydrocarbyl-3,3-bis(hydroxyaryl)phthalimidine composition of claim 19, wherein 2-hydrocarbyl-3,3-bis(hydroxyaryl)phthalimidine composition comprises less than 100 ppm of an amino phenol, 2-aryl-3-(aminoaryl-3-(hydroxyaryl)phthalimidine of formula (8) and less than 100 ppm of 2-phenyl-3-(4-hydroxyphenyl)-3-(2-hydroxyphenyl)phthalimidine of formula (7)

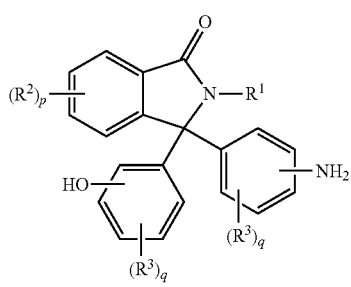

(8)

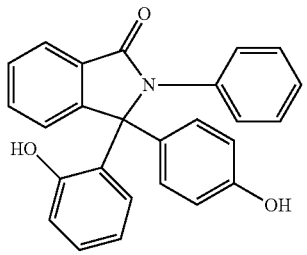

(7)

wherein
$R^1$ is $C_{1-6}$ alkyl, $C_{1-6}$ alkoxy, or phenyl optionally substituted with 1 to 5 $C_{1-6}$ alkyls,
each occurrence of $R^2$ and $R^3$ is independently a $C_{1-6}$ alkyl, and
p and q are each independently 0 to 4.

22. The polycarbonate of claim 20, wherein polycarbonate comprises less than 100 ppm of an amino phenol, 2-aryl-3-(aminoaryl-3-(hydroxyaryl)phthalimidine of formula (8) and less than 100 ppm of 2-phenyl-3-(4-hydroxyphenyl)-3-(2-hydroxyphenyl)phthalimidine of formula (7)

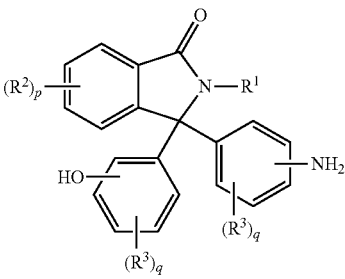

(8)

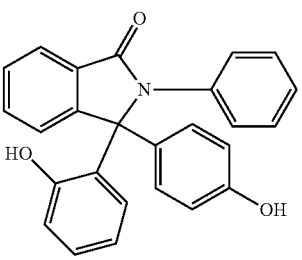

(7)

wherein
$R^1$ is $C_{1-6}$ alkyl, $C_{1-6}$ alkoxy, or phenyl optionally substituted with 1 to 5 $C_{1-6}$ alkyls,
each occurrence of $R^2$ and $R^3$ is independently a $C_{1-6}$ alkyl, and
p and q are each independently 0 to 4.

23. The method of claim 1, wherein the catalyst is $AlCl_3$.

* * * * *